US009162255B1

(12) United States Patent
Stice et al.

(10) Patent No.: US 9,162,255 B1
(45) Date of Patent: Oct. 20, 2015

(54) TUNABLE ULTRASOUND TRANSMITTER

(75) Inventors: John R. Stice, Seattle, WA (US);
Yanwei Wang, Bothell, WA (US);
Clinton T. Siedenburg, Everett, WA (US); Andrew K. Lundberg, Woodinville, WA (US); Justin Coughlin, Seattle, WA (US); Max E. Nielsen, Smithfield, UT (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 843 days.

(21) Appl. No.: 12/686,685

(22) Filed: Jan. 13, 2010

(51) Int. Cl.
*B06B 1/02* (2006.01)
*A61B 8/00* (2006.01)

(52) U.S. Cl.
CPC ............... *B06B 1/0207* (2013.01); *A61B 8/44* (2013.01); *A61B 8/4444* (2013.01); *B06B 1/023* (2013.01); *B06B 1/0215* (2013.01); *B06B 1/0223* (2013.01)

(58) Field of Classification Search
CPC .. B06B 1/0207; B06B 1/0215; B06B 1/0223; B06B 1/023; A61B 8/4444; A61B 8/4483; A61B 8/44
USPC .................................................. 600/437, 459
See application file for complete search history.

(56) References Cited

U.S. PATENT DOCUMENTS

| 3,900,823 | A  | * | 8/1975 | Sokal et al. ..................... 330/149 |
| 4,173,007 | A  | * | 10/1979 | McKeighen et al. ........... 367/11 |
| 6,206,833 | B1 |   | 3/2001 | Christopher |
| 7,004,905 | B2 |   | 2/2006 | Christopher |
| 7,104,956 | B1 |   | 9/2006 | Christopher |
| 2004/0113669 | A1 | * | 6/2004 | Wodnicki ....................... 327/170 |
| 2008/0009744 | A1 | * | 1/2008 | Misono .......................... 600/462 |
| 2009/0167436 | A1 | * | 7/2009 | Ardehali ........................ 330/251 |

FOREIGN PATENT DOCUMENTS

JP   2002-315749   * 10/2002

OTHER PUBLICATIONS

Katsuki et al., "Higher-Harmonic Distortion Canceller Using a Switching Amplifier with Minimum Output Power", Telecommunications Energy Conference, INTELEC '95, 17th International, pp. 235-242, 1995.*
English translation of JP 2002-315749 as provided by AIPN translation tool.*
T. Sato et al., "Nonlinear Tissue Imaging," 1986 Ultrasonics Symposium, 0090-5607/86/0000-889, 1986 IEEE, pp. 889-900.
Edited by Keith Y. Wang, University of Houston, Houston, Texas, Plenum Press, New York and London, Acoustical Imaging, vol. 9, Visualizatin and Charaterization, 12 pages.
U.S. Appl. No. 12/762,019, Hwang et al.
U.S. Appl. No. 12/467,899, Hwang et al.

* cited by examiner

*Primary Examiner* — Katherine Fernandez
(74) *Attorney, Agent, or Firm* — Perkins Coie LLP

(57) ABSTRACT

The use of power-efficient transmitters to establish acoustic wave energy having low undesirable harmonics is achieved by adjusting the transmitter output waveform to minimize the undesirable harmonics. In one embodiment, both the timing and slope of the waveform edges are adjusted to produce the desired output waveform having little or no second harmonics. In the embodiment, output waveform timing adjustments on the order of fractions of the system clock interval are provided. This then allows for very fine control of a coarsely produced waveform. In one embodiment, the user can select the fine tuning to match the transmitter output signal to a particular load transducer.

3 Claims, 5 Drawing Sheets

TUNABLE ULTRASOUND TRANSMITTER

TECHNICAL FIELD

This disclosure relates to acoustic signal transmitters and more particularly to such transmitters having one or more tunable attributes for controlling harmonics.

BACKGROUND OF THE INVENTION

Ultrasound imaging has been utilized for years to view features and structures obfuscated by overlying material, surfaces, etc. For example, ultrasound systems are commonly used to provide imaging of subsurface tissue and features (e.g., blood flow) in the human body.

Tissue Harmonic Imaging, "THI," is a technique used in sonography to provide high quality images. THI relies on a phenomena whereby biological tissues (and/or other media) react to illumination by an acoustic wave (e.g., an ultrasound wave generated by an ultrasound imaging system) by generating second-order harmonics of the acoustic wave. Such tissue-generated second-order harmonics stem from the compression and decompression of tissue impacted by energy from acoustic sound waves transmitted into, or illuminating, the tissue. The resulting second-order harmonic signals propagate through the tissue and may thus be received by the acoustic transceiver of an ultrasound system. THI techniques utilize the received second-order harmonic signals to generate high quality images, such as to provide sharp edges, reduced clutter, etc. within the generated image. Harmonics higher than second-order are usually unimportant according to THI techniques because higher frequency harmonics rapidly attenuate as they propagate. Although higher order even harmonics could be used if desired, odd harmonics are not typically generated by the subject tissue and thus are typically ignored by THI techniques.

Because THI techniques rely upon the second-order harmonics generated by the tissue to generate the image, it is important that the acoustic wave illuminating the tissue be relatively free of second-order harmonics. That is, the presence of second-order harmonics not generated by the subject tissue may be emitted or created by the ultrasound system acoustic transceiver and electronics and degrade the quality of the image, such as by causing image clutter, decreasing edge sharpness, etc.

For example, according to the THI technique referred to as the "filter method," the ultrasound system's receivers are frequency optimized (e.g., through combinations of both digital signal processing and receiver resonance) to the second harmonic of the acoustic wave. The resulting received second harmonic signals are processed into an image. In this technique, it is important to limit the amount of second-order harmonics generated within the transmitter as these harmonics interfere with the tissue-generated harmonics.

According to the THI technique referred to as "pulse inversion," two successive ultrasound bursts are transmitted with the second burst being an inversion of the first burst. That is, mathematically speaking, the second burst is precisely equal to the first burst except that it is multiplied by −1. To receive the reflected signals, the ultrasound receivers remain broadband and tuned to both the fundamental frequency and the second-order harmonic. Signals received from the first ultrasound burst are summed with signals received from the second burst. To perform this summing, both received signals are first aligned in time and are then summed (e.g., using digital techniques). The concept here is that if the two successive transmitter bursts are exactly equal but inverted, the summing of the resulting received signals will cancel except for tissue generated second-harmonics which are then processed into an image. The even-order harmonics generated by the tissue are not cancelled by the foregoing summing because the harmonic signals are generated in-phase, rather than with an inversion. In order for the pulse inversion THI technique to be effective, the paired burst signals must be equal and opposite, which has proven to be very difficult without implementing very complex circuits and/or highly linear transmitters.

Linear transmitter electronics utilized to minimize the second-order harmonics generated by ultrasound system acoustic transceivers apply a high amplitude sine wave to the acoustic elements of the acoustic transceiver and the acoustic elements respond by generating an acoustic signal (the acoustic signals from a plurality of acoustic elements combining to form an acoustic wave) having a low harmonic level. A problem with using this approach, however, is that it results in high power dissipation, mostly by heat in the electronics rather than by the power being transferred to the acoustic element. That is, transmitter circuits utilized to provide the high amplitude sine wave are somewhat inefficient resulting in appreciable amounts of energy being converted into heat rather than being applied to the acoustic elements for acoustic signal generation. This then has several negative effects, including thermal management problems and, in the case of a battery powered instrument, rapid battery depletion.

Techniques to limit second-order harmonic generation, without incurring linear transmitter power dissipation penalties, have also been tried. For example, techniques such as pulse-width modulation and stepped application of transmitters operating at different supply voltages have been employed. These techniques at the present state of the art, however, have not been found to be particularly advantageous because of their circuit complexity and the lack of adequate, extremely fast power switching devices.

BRIEF SUMMARY OF THE INVENTION

The present invention is directed to systems and methods which implement power-efficient transmitters to generate acoustic waves having low undesirable harmonics (e.g., second-order harmonics) through tuning the transmitter output waveform to minimize the undesirable harmonics. In one embodiment, transmitter output waveform tuning is provided by adjusting the timing and/or slope of the transmitter output waveform edges to produce a transmitter output waveform, for driving acoustic elements, having little or no second harmonics associated therewith.

Embodiments of the invention provide a simplified and efficient implementation wherein a system clock is utilized for providing timing with respect to transmitter output waveform edges. Programmable circuitry is utilized according to embodiments to provide timing adjustment of the transmitter output waveform edges on the order of fractions of the system clock interval. For example, programmable sub-clock cycle programmable delay circuitry may be utilized to adjust the timing of one or more transmitter output waveform edges. Additionally or alternatively, programmable circuitry is utilized according to embodiments to provide slope adjustment of the transmitter output waveform edges. For example, programmable pull-down transistor circuitry may be utilized to adjust the slope of one or more transmitter output waveform edge. Such embodiments allow for very fine control of an otherwise coarsely produced transmitter output waveform.

In operation according to embodiments of the invention, the foregoing tuning of the transmitter output waveform is implemented to reduce the amount of second-order harmonics associated with the transmitter output waveform, such as by providing a close match to the response of acoustic elements of acoustic transceivers. Additionally or alternatively, the foregoing tuning of the transmitter output waveform is implemented to generate precisely matched inverted and non-inverted waveforms inverse waveforms, such as for use in a pulse inversion technique.

The foregoing has outlined rather broadly features and technical advantages of the present invention in order that the detailed description of the invention WHICH follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

Figure 1:
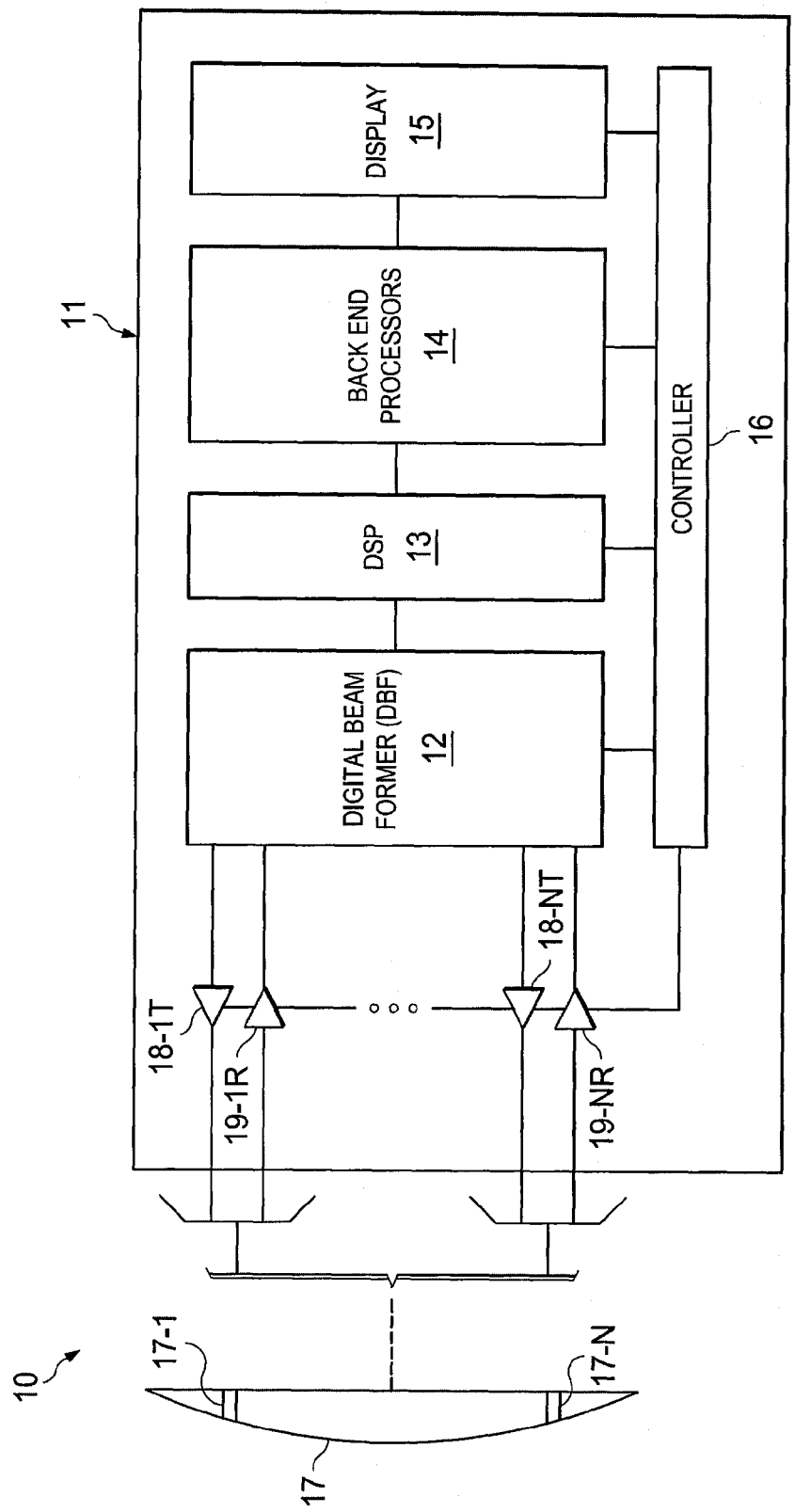
FIG. 1 is a block diagram of a sonogram system utilizing the concepts of the present invention.

FIG. 1 shows one embodiment of an ultrasound system adapted according to embodiments of the invention. Ultrasound system 10 of the illustrated embodiment comprises an acoustic transceiver or transducer, shown as transducer 17, in electrical communication with a system unit, shown as system unit 11, operable to transmit and receive ultrasound signals for sonographic image generation.

Transducer 17 includes a plurality of transducer elements (e.g., acoustic elements), shown as elements 17-1 to 17-N. A variety of transducer element configurations will work with the concepts discussed herein. For example, elements 17-1 to 17-N may each comprise a piezoelectric crystal, a micromachined transducer, an electromagnetic transducer, etc. Elements 17-1 to 17-N (together with their transmission line) will typically present a mathematically complex impedance, wherein mathematically complex in this context means that the impedance has a real component and an imaginary component. It should be appreciated that it is difficult to efficiently drive reactive elements having complex impedance, such as elements 17-1 to 17-N, and achieve low harmonics.

In operation, elements 17-1 to 17-N, or some subset thereof, are energized in the transmit phase by corresponding transmitters, shown as transmitters 18-1T to 18-NT, to generate acoustic signals. The acoustic signals from a plurality of acoustic elements are controlled (e.g., beamformed) to create an acoustic wave for illuminating one or more targets (e.g., tissue of interest). Acoustic signals resulting from illumination of the target (e.g., reflected acoustic signals, harmonic signals generated by illuminated tissue, etc.) are received and converted to electrical signals by elements 17-1 to 17-N. These electrical signals are provided from transducer 17 to corresponding receivers, shown as receivers 19-1R to 19-NR, of system unit 11 for processing and image generation by additional circuitry of system unit 11.

In addition to the aforementioned transmitters and receivers, system unit 11 of the illustrated embodiment includes digital beamformer (DBF) 12, digital signal processor (DSP) 13, back end processors 14, and display 15. DBF 12, DSP 13, and back end processors 14 may comprise various configurations of circuitry and/or logic. For example, application specific integrated circuits (ASICs), field programmable gate arrays (FPGAs), general purpose processor-based systems operable under control of an instruction set, and/or the like may be utilized in providing DBF 12, DSP 13, and back end processors 14. Display 15 may comprise various configurations of user interface devices, such as liquid crystal display (LCD), cathode ray tube (CRT), plasma display, touch screen, etc.

DBF 12 of embodiments provides analog to digital signal conversion, signal multiplexing, signal beamforming, and/or signal buffering between transducer 17 and other circuitry of system unit 11. Image processing with respect to received signals is controlled according to embodiments by the combination of DSP 13 and back end processors 14. Display 15 of the illustrated embodiment provides display of the generated images. In the embodiment shown, controller 16 operates to control the overall operation of ultrasound system 10. Additional detail with respect to the general operation of ultrasound systems is provided in co-pending U.S. patent application Ser. No. 11/762,019 filed Jun. 12, 2007, entitled "Ultrasonic Signal Processor For a Hand Held Ultrasonic Diagnostic Instrument," and Ser. No. 12/467,899 filed May 18, 2009, entitled "Modular Apparatus for Diagnostic Ultrasound," the disclosures of which are incorporated herein by reference.

It should be appreciated that the illustrated embodiment of ultrasound system 10 provides one example of an ultrasound system configuration. The concepts discussed herein are applicable with respect to any number of system configurations and thus are not limited to application with respect to ultrasound system 10.

Ultrasound system 10 of the illustrated embodiment is adapted to generate acoustic waves having low undesirable harmonics. In particular, transmitters 18-1T through 18-NT of embodiments comprise tunable, power-efficient transmitters adapted for generating acoustic waves having low undesirable harmonics (e.g., second-order harmonics). For example, transmitter output waveform tuning is provided according to embodiments of transmitters 18-1T through 18-NT by adjusting the timing and/or slope of the transmitter output waveform edges to produce a transmitter output waveform, for driving acoustic elements, having little or no second harmonics associated therewith.

Figure 2A:
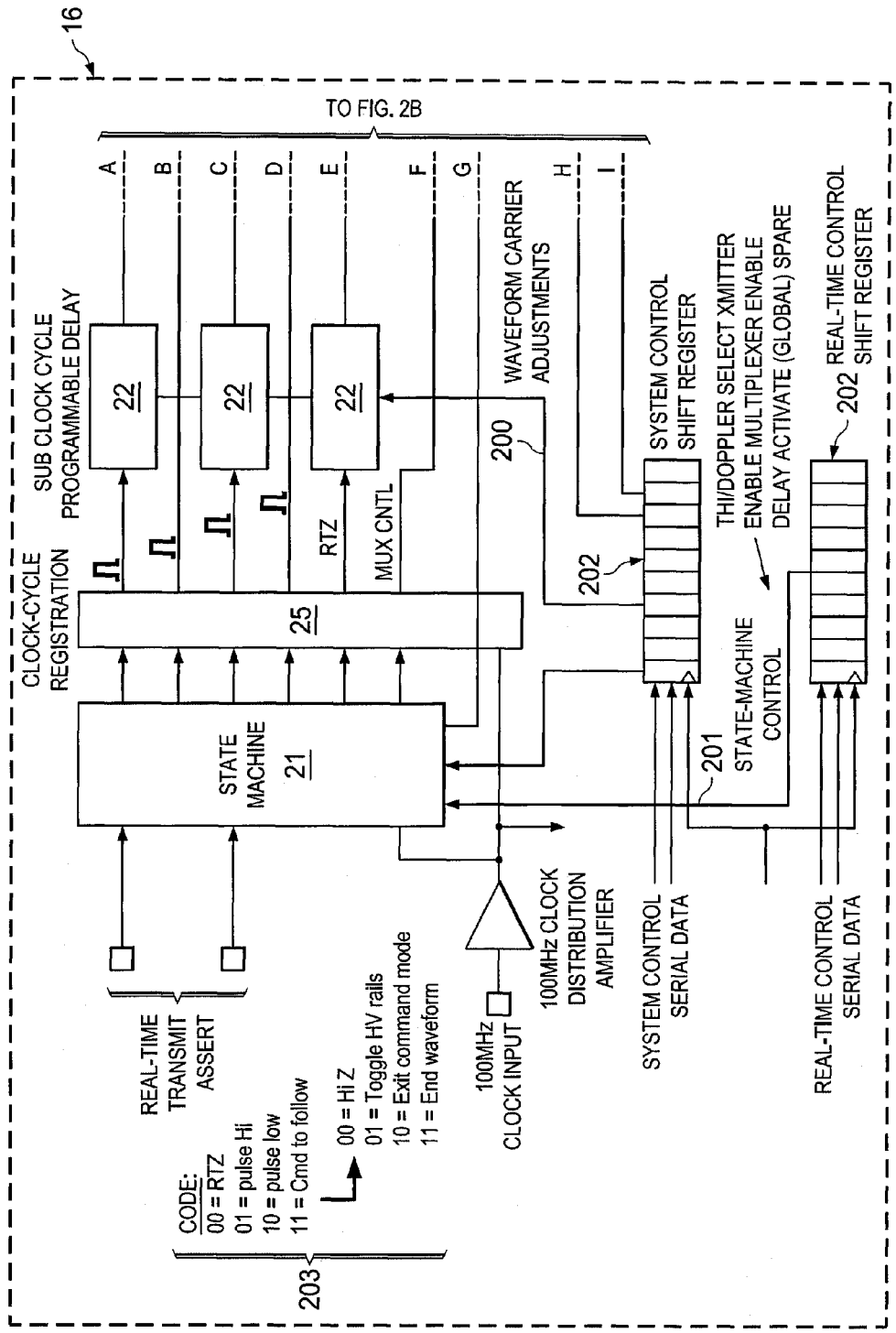
FIGS. 2A and 2B show one embodiment of a transmitter and control circuit in accordance with the teachings of the inventive concepts herein.
Figure 2B:
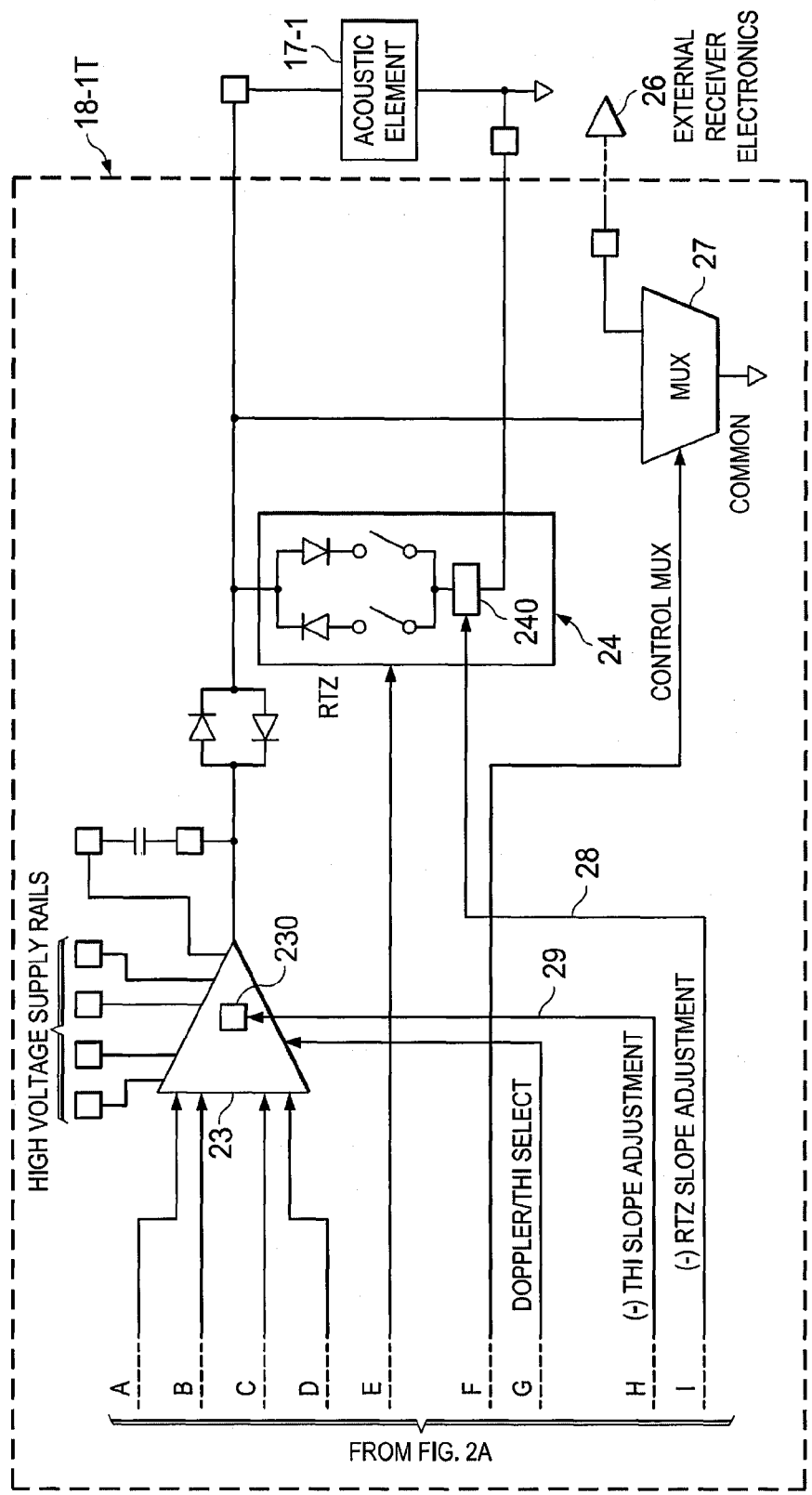

FIGS. 2A and 2B show additional detail of an embodiment of controller 16 and transmitter 18-1T providing a tunable, power-efficient transmitter configuration adapted for generating acoustic waves having low undesirable harmonics. It should be appreciated that, although only transmitter 18-1T is shown for clarity and to simplify the discussion, the transmitter circuitry of all of transmitters 18-1T to 18-NT are similarly configured and provided control by controller 16 according embodiments of the invention. It should further be understood that FIG. 2A shows only a portion of controller 16 relevant to the discussion of the tunable transmitter embodiment described, and thus controller 16 of FIG. 1 may include additional circuitry relevant to providing control with respect to other aspects of ultrasound system 10.

Transmitter 18-1T of the embodiment shown in FIG. 2B includes amplifier 23 used in providing a transmitter output waveform of sufficient amplitude to energize corresponding acoustic element 17-1. Amplifier 23 controls the energy delivered to the acoustic element by providing an output whose amplitude is established by the high voltage supply rails, for example. During a sonographic system's transmit phase, high voltage signals from amplifier 23 are applied to the acoustic elements. These high voltages may be isolated from the sensitive receiver electronics (e.g., DBF 12, DSP 13, and back end processors 14 represented by external receiver electronics 26 in FIG. 2B) by a transmit/receive multiplexer (MUX) (e.g., MUX 27 in FIG. 2B). In operation, at the conclusion of the transmit burst, the multiplexer connects the acoustic element to the receiver electronics so that received acoustic waves can be processed electronically. Conversely, at the conclusion of the receive interval, the multiplexer disconnects the receiver electronics from the acoustic element in preparation for the next transmit burst.

In order to provide a power efficient implementation, amplifier 23 of embodiments comprises a switching amplifier such as a class C amplifier. Class C amplifiers operate by switching their load between two or more power supply voltages using low resistance electronic switches (usually transistors) to efficiently transfer energy from the power supplies (e.g., the high voltage supply rails) to the load (e.g., acoustic element 17-1). Unlike a linear amplifier, there is no voltage differential across a class C amplifier between its power supply input terminal and its output terminal since its output is momentarily shorted to a power supply input through the amplifier's low impedance switching elements. Thus, there is essentially zero voltage between the power supply input terminal of the class C amplifier and the output of the class C amplifier, providing a very power efficient amplifier configuration. Specifically, even though substantial amounts of current may be flowing through the amplifier, the product of this current times the voltage difference across the amplifier circuit (which is almost zero) remains very small thereby resulting in low power dissipation in the amplifier.

It should be appreciated that, although embodiments are described herein with reference to class C amplifiers, the concepts herein are applicable with respect to other circuit configurations. For example, the concepts herein may be applied with respect to various switching amplifier circuit configurations, class D amplifier circuit configurations, radio transmitter circuit configurations, and the like.

By controlling selection of the particular high voltage supply rails used to drive the output of amplifier 23, various transmitter output waveforms may be provided. For example, using a positive high voltage supply rail (e.g., +28 Volts) and a corresponding negative high voltage supply rail (e.g., −28 Volts), amplifier 23 may be controlled to provide a transmitter output waveform in the form of a square wave. Such a square wave transmitter output waveform is shown as transmitter output waveform 31 in FIG. 3. Although the foregoing square wave transmitter output waveform provides very efficient power transfer into the acoustic element with very little power dissipation in the transmitter electronics, such output is typically rich in harmonics and thus is problematic for use in THI applications.

Figure 3:
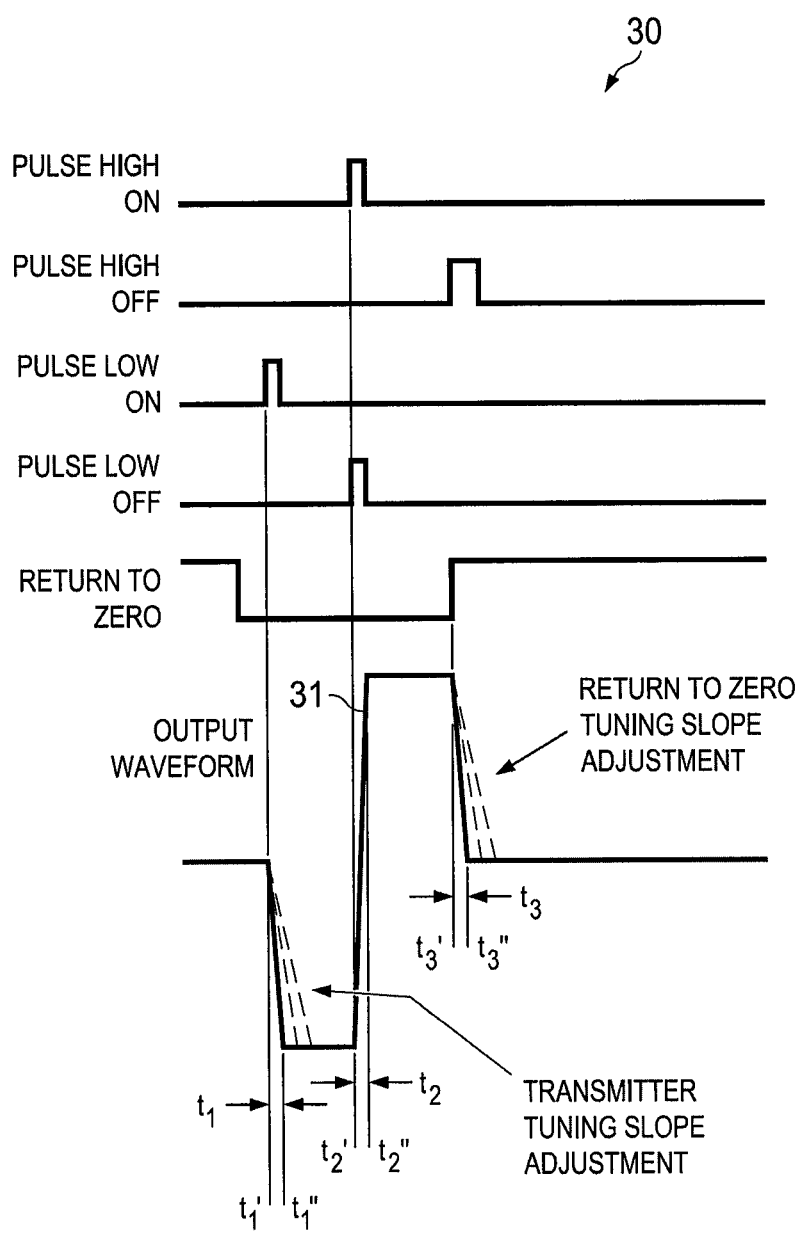
FIGS. 3 and 4 show graphs of transmitter output waveforms for harmonic control according to the concepts herein.

Accordingly, controller 16 and transmitters 18-1T through 18-NT are adapted to implement tuning techniques to generate acoustic waves having low undesirable harmonics. Tuning techniques implemented according to embodiments of the invention provide adjustment of the timing and/or slope of the transmitter output waveform edges, as illustrated in FIG. 3.

As can be seen by the relationship of timing graph 30 to transmitter output waveform 31, transmitter output waveform 31 of the illustrated embodiment is controlled by signal pulses commanding amplifier 23 to either go high or to go low, wherein the transmitter output waveform amplitude is established by the high voltage supply rails and the gain factor of amplifier 23. Return to zero (RTZ) is a signal level controlling the transmitter output's connection to "common". Time periods t1 (the time between time t1' and t1"), t2 (the time between time t2' and t2"), and t3 (the time between time t3' and t3") define the output waveform's shape or "corners" and harmonics of the output waveform are associated with these times. Accordingly, adjustment of one or more of these times, and thus a rate of change (slope) associated therewith, is utilized according to embodiments of the invention for minimizing second-order harmonics. For example, the foregoing tuning of the transmitter output waveform is implemented to provide a transmitter output waveform adapted to match the complex impedance of the acoustic elements. Additionally or alternatively, the foregoing tuning of the transmitter output waveform is implemented to provide precise adjustment of the slopes of the output waveform so as to form a match between a pulse-inverted waveform and a non-inverted waveform (as shown by pulse-inverted waveform 42 and non-inverted waveform 41 of FIG. 4).

Controller 16 of the embodiment illustrated in FIGS. 2A and 2B provides control of output waveform timing (e.g., timing of times t1', t2', and t3') and transmitter output waveform slope adjustment (e.g., duration of time periods t1, t2, and t3) to implement tuning techniques herein. State machine 21, for example, is utilized to provide control of output waveform timing. According to embodiments, there will be one such state machine per transmitter of ultrasound system 10.

State machine 21 may take logic control signal input from one or more external sources. For example, the illustrated embodiment of state machine 21 utilizes input from a digitally pre-compiled wave table, shown as table 203, having values stored in system memory. Such a pre-compiled wave table is particularly advantageous because it allows arbitrary, complex transmitter waveforms to be pre-determined during the ultrasound system's design and during factory assembly, or at other points in the life of ultrasound system 10. Additionally or alternatively, control signals utilized by state machine 21 may be taken from logic shift registers, shown as shift registers 202, via control signals 201. Such shift registers are a very efficient means of loading multiple control signals into devices which implement an array of transmitters, such as ultrasound system 10 (e.g., an array of transmitters and their associated controllers may utilize multiple and unique control signals for each transmitter in providing a desired operational mode).

In operation of state machine 21 of the illustrated embodiment to provide control of timing of the transmitter output waveform, the digital control signals provided by external wave table 203 are clocked out of the wave table on a system clock cycle. In accordance with the particular configuration defined by external wave table 203, state machine 21 supplies waveform control pulses using clock cycle registration 25.

The waveform control pulses are used to drive the edges of the transmitter output waveform. Specifically, the illustrated embodiment of state machine 21 provides a pulse (A) that turns amplifier 23 on to a positive high voltage supply rail (corresponding to "pulse high on" of FIGS. 3 and 4), a pulse (B) that turns amplifier 23 off of the positive high voltage supply rail (corresponding to "pulse high off" of FIGS. 3 and 4), a pulse (C) that turns amplifier 23 on to a negative high voltage supply rail (corresponding to "pulse low on" of FIGS. 3 and 4), a pulse (D) that turns amplifier 23 off of the negative high voltage supply rail (corresponding to "pulse low off" of FIGS. 3 and 4), and a pulse (E) that returns the transmitter output waveform to common (corresponding to "return to zero" of FIGS. 3 and 4).

According to embodiments of the invention, the first four of the above pulses (A-D) are utilized to control the transmitter output waveform by controlling the output of amplifier 23, while the fifth pulse (E) is utilized to control the timing of RTZ circuit 24. The RTZ pulse controls the timing of the transmitter output waveform as the transmitter output waveform is brought from one of the high voltage supply rails (either a high supply rail or a low supply rail) back to zero volts (common). Specifically, RTZ circuit 24 operating in accordance with the RTZ pulse (E) clamps the transmitter output waveform to system common so as to rapidly quench any ringing which may be present at the conclusion of an acoustic element driving cycle.

The above described operation of state machine 21 quantizes the waveform control pulses to the system clock interval. That is, the state machine of the illustrated embodiment, by virtue of being logic operated by a system clock, outputs the amplifier control signal pulses in synchronization with that system clock. However, a transmitter output waveform quantized to the system clock interval is not necessarily acceptable for low harmonic performance. Therefore, operation according to the illustrated embodiment provides adjustment at a sub-clock cycle level to these waveform control pulses using delay lines 22.

Delay lines 22 of the illustrated embodiment may comprise digital and/or analog signal delay circuitry adapted to provide precise adjustment of waveform control pulses (e.g., by adjusting the timing of times t1', t2', and/or t3') used to generate the transmitter output waveform. Although the system clock cycle based waveform control pulse granularity provided by state machine 21 may be inadequate to provide the degree of control desired to appropriately adjust waveform control pulse timing for minimizing harmonics, the sub-clock cycle intervals available from delay lines 22 provide suitable granularity according to embodiments of the invention. For example, delay lines 22 may each comprise a plurality of selectable delays (e.g., a binary ladder of selectable delays) which may be selected individually or in combination to provide a desired amount of delay. Delay provided by delay lines 22 may each be individually selected by logic signal levels provided from shift registers 202. For example, the propagation delay introduced by delay lines 22 may be controlled by a bit pattern supplied by shift registers 202 via control signals 200, whereby bit patterns from shift registers 202 are applied individually to the delay lines. In the case of particular waveform control pulses which are not tuned, appropriate ones of delay lines 22 may be switched out (deactivated) by the control signals.

In operation according to the illustrated embodiment, the waveform control pulses provided by state machine 21, which are quantized to the system clock timing, are routed through delay lines 22, which are set to provide individual adjustment of the waveform control pulses for precise timing of the pulses as they are applied to amplifier 23. This allows for precise adjustment of the corners of the transmitter output waveform to minimize harmonics according to embodiments of the invention. As illustrated in timing graphs 30 and 40 of FIGS. 3 and 4, the timing of the foregoing waveform control pulses determines the edges of the transmitter output waveform. The edges of the transmit output waveform are important for second harmonic considerations.

In operation of controller 16 of the embodiment illustrated in FIGS. 2A and 2B to provide control of timing of the transmitter output waveform, transmitter output waveform slope (rate of change) adjustment control (e.g., control of time periods t1, t2, and/or t3) is provided with respect to amplifier 23 and RTZ circuit 24. For example, according to the illustrated embodiment amplifier 23 will pull up to the positive high voltage supply rail as strongly as it can. In order to minimize harmonics, it is desirable that when amplifier 23 pulls to the negative high voltage supply rail it does so with the rate of change of the output voltage for the negative going slope being equal to the rate of change of the voltage that goes to the positive supply rail. The positive slope (the rate of change of voltage going from zero up to the positive supply rail) is a fixed quantity in the illustrated embodiment. However, the negative slope (the rate of change of the voltage going from zero down to the negative supply rail) may be adjusted so that it can be precisely made equal to the positive going rate of change. Adjustment of the negative slope provided by RTZ circuit 24 (the rate of change of the voltage going from the positive supply rail to zero) may be similarly controlled. Alternative embodiments of the invention may accomplished such slope matching the other way around (i.e., by holding the negative rate slope at what it is and adjusting the positive slope). A goal, according to embodiments, is to balance the positive with the negative slopes so that when pulse-inversion THI is used, the slopes will cancel.

Figure 4:
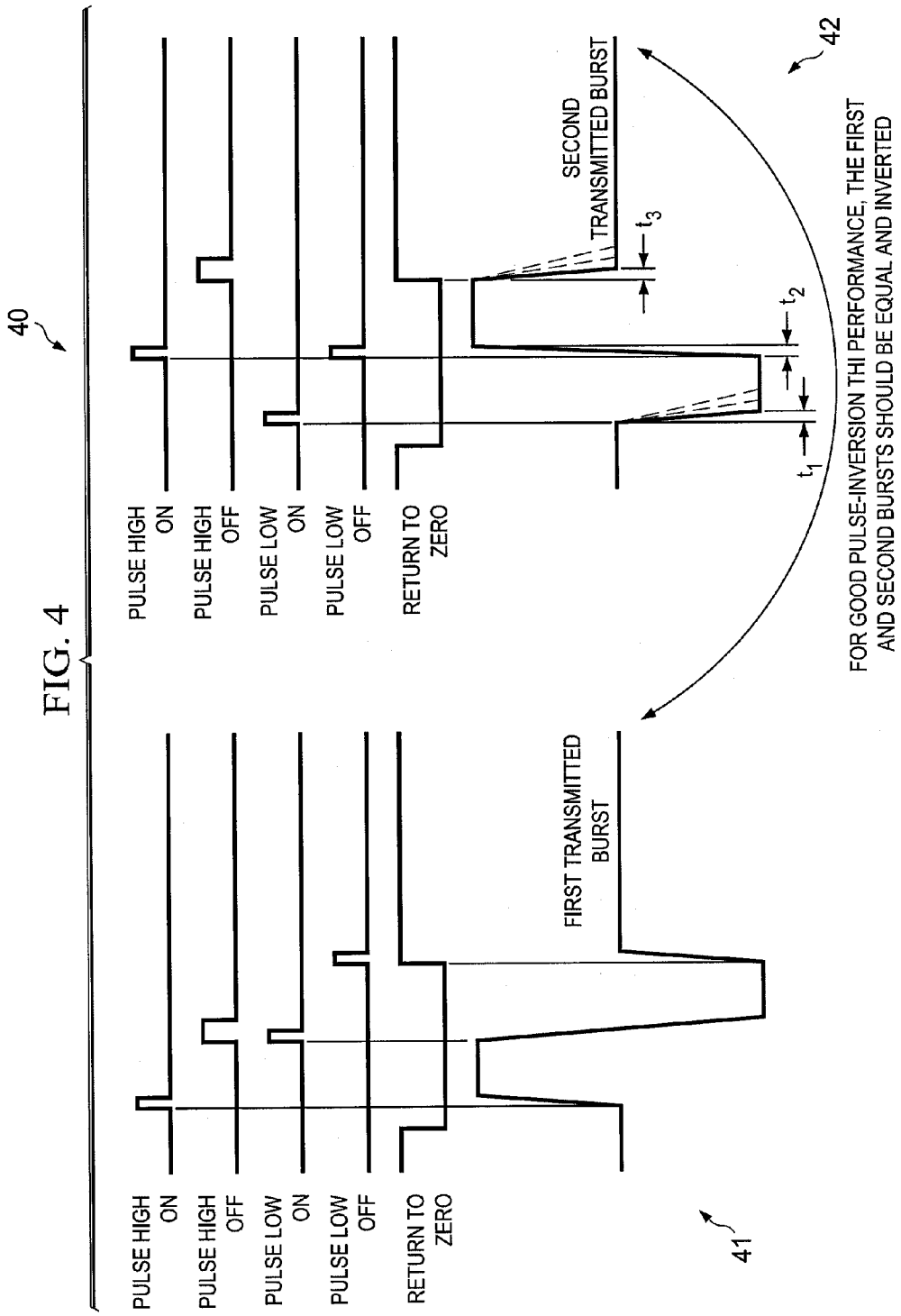

According to embodiments, the slope of a portion of the transmitter output waveform associated with amplifier 23 transitioning to a low output can be adjusted under control of certain bits in shift registers 202 (control signal 29). Similarly, the slope of a portion of the transmitter output waveform associated with RTZ circuit 24 transitioning the transmitter output waveform to zero can be adjusted under control of certain bits in shift registers 202 (control signal 28). Such adjustment of transmitter output waveform slopes is particularly useful with respect to pulse inversion THI techniques, whereby the adjustments may be made to match the slope of a negative going slope of a pulse-inverted waveform with a corresponding positive going slope of a non-inverted waveform, as shown in FIG. 4. In this manner, second-order harmonics associated with the transmitter output waveform may be minimized.

To facilitate at least one of the foregoing adjustable transmitter output waveform slopes, amplifier 23 of embodiments includes one or more transistors disposed in a pull-down configuration, shown as pull-down transistors 230 in FIG. 2B, to control the rate at which a signal output by amplifier 23 goes low. For example, amplifier 23 may comprise a totem pole, high voltage, N-DMOS output stage having a large N-DMOS high voltage transistor between the positive supply rail and the output, and binary weighted high voltage N-DMOS transistors between the output and the negative supply rail to provide the aforementioned pull-down transistor configuration. To facilitate at least one of the foregoing adjustable transmitter output waveform slopes, RTZ circuit 24 of embodiments includes one or more transistors disposed in a pull-down configuration, shown as pull-down transistors 240 in FIG. 2B, to control the rate at which a signal output by RTZ circuit 24 goes to zero. For example, RTZ circuit 24 may comprise a P-DMOS transistor used as a pull up device, along with binary weighted N-DMOS transistors to provide the aforementioned pull-down transistor configuration.

Control signals 28, such as may comprise digital control signals, operate to adjust the strength of the pull-down transistors of RTZ circuit 24 to thereby control the RTZ negative-going slope, as shown in FIG. 3. Pull-down transistor strength is selected according to embodiments by virtue of control signals 28 enabling (as opposed to activating) binary-weighted pull-down transistors in RTZ circuit 24. Pull-down transistor activation (of the appropriately enabled transistors) is set by the "return to zero" waveform control pulse (pulse E) provided by state machine 21, as described above.

Control signals 29, such as may comprise digital control signals, operate to adjust the strength of the pull-down transistors of amplifier 23 to thereby control the amplifier's negative-going slope, as shown in FIG. 3. Pull-down transistor strength is selected according to embodiments by virtue of control signals 29 enabling (as opposed to activating) binary-weighted pull-down transistors in amplifier 23. Pull-down transistor activation (of the appropriately enabled transistors) is set by the "pulse low on" waveform control pulse (pulse C) provided by state machine 21, as described above.

The foregoing pull-down transistor strengths are made adjustable according to embodiments by means of preferentially switching in pull-down transistors whose strength is a binary weight. One example uses four transistors that are binary weighted to yield a total of 16 different possible pull-down transistor strengths, any of which can be selected to adjust the negative slopes as discussed above. Note that other arrangements of controlling pull-down strength can be used, if desired.

FIG. 4 shows the effect of tunable transmitter operation with respect to two pulses transmitted using the pulse-inversion method discussed herein. Transmitter output waveform 41 shows the first pulse burst and transmitter output waveform 42 shows the second, inverted pulse burst. The first burst is "positive-onset" and the second is "negative-onset," though this is arbitrary in the example. According to an embodiment, the first burst is transmitted with the transmitter electronics, including RTZ, set to an arbitrary nominal or baseline configuration. The second, inverted burst, is transmitted with the transmitter electronics, including RTZ, "tuned" so as to equal or match the first burst. The particular adjustments made to the second burst may be arrived at during an initial circuit calibration, in real-time during operation (e.g., using suitable software control algorithms), etc.

From the foregoing, it can be appreciated that ultrasound system 10 having tunable transmitters 18-1T to 18-NT operates, as discussed above, to reduce the second harmonic associated with a given transmitter output waveform. In particular, according to embodiments there are several things being done to minimize second-order harmonics. For example, the timing of the transmitter output waveform is being adjusted through the analog delay lines. Additionally, the slope of portions of the transmitter output waveform are being asymmetrically adjusted. Accordingly, the tunable transmitter configuration may be controllable to provide exact, or nearly exact, inverse waveforms for implementing pulse inversion techniques. Additionally or alternatively, the tunable transmitter configuration of embodiments is operable to tune the transmitter output waveform for different loads such that the transmitter, the performance of which depends on the load being transmitted into, is well adapted to good performance on a large variety of different loads. Implementation of state machine 21 of embodiments allows the transmitter configuration to operate with lower power than otherwise since power is used primarily on the clock transitions as opposed to the whole duty cycle of the clock.

The concepts discussed herein further accommodate the minimization of the number of controls used to control the transmitter output waveforms. This has been accomplished, in part, because one of the transmitter output waveforms is left unadjusted in one polarity and thus only the controls utilized to match the inverted waveform to the paired transmitter output waveform are provided. Moreover, the particular edges of the transmitter output waveform for which adjustment is provided have been selected to minimize the total number of control edges while still maintaining the ability to obtain the best match possible.

It should be noted that the various pulse and transmitter waveform output patterns represented in the figures are arbitrary and are present for example only. Accordingly, the concepts of the present invention may be applied with respect other patterns, as desired.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A transmitter circuit for delivering energy to a transducer element, the circuit comprising:
  a switching amplifier configured to produce an output that forms at least a portion of a transmitter output waveform including positive and negative going pulses for delivery to the transducer element, wherein the switching amplifier includes a first high power transistor connected between the output of the amplifier and one of a positive or a negative high voltage rail and a number of binary-weighted transistors connected between the output of the amplifier and the other of the negative or positive high voltage rail, wherein the binary-weighted transistors are selectively enabled by a control signal to adjust a rate of change of a voltage transition at the output of the amplifier to match a rate of change of a voltage transition produced by the first high power transistor;
  a controller coupled to the switching amplifier, wherein the controller is configured to output the control signal to the binary-weighted transistors and further configured to output control pulses for tuning the positive and negative going pulses, wherein the control pulses are synchronized with a system clock; and
  a number of selectable delay lines each of which is connected to receive a control pulse from the controller and configured to provide a selectable delay of the control pulse by sub-clock intervals to adjust corners of a positive or negative going pulse to match those of a previously produced negative or positive going pulse.

2. The circuit of claim 1, wherein the switching amplifier comprises a class C switching amplifier.

3. The circuit of claim 1, further comprising:
a return to zero circuit configured to produce at least a portion of the transmitter output waveform, wherein the return to zero circuit comprises a transistor circuit having a number of binary-weighted transistors, and wherein a slope of a voltage transition of the transmitter output waveform from the positive or negative high voltage rail to zero is controlled by the controller providing control signals to enable selected ones of the number of binary-weighted transistors of the transistor circuit.

* * * * *